(12) United States Patent
Wolkin et al.

(10) Patent No.: US 7,816,146 B2
(45) Date of Patent: Oct. 19, 2010

(54) PASSIVE ELECTRONIC DEVICES

(75) Inventors: Michal V. Wolkin, Los Altos, CA (US); Ana C. Arias, San Carlos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 1154 days.

(21) Appl. No.: 11/318,967

(22) Filed: Dec. 27, 2005

(65) Prior Publication Data
US 2007/0145362 A1      Jun. 28, 2007

(51) Int. Cl.
*G01N 25/20*       (2006.01)
(52) U.S. Cl. .......................... 436/147; 422/51; 422/68.1
(58) Field of Classification Search .................. None
See application file for complete search history.

(56) References Cited

U.S. PATENT DOCUMENTS

| | | | |
|---|---|---|---|
| 4,731,340 A | 3/1988 | Chang et al. | |
| 4,863,808 A | 9/1989 | Sallo | |
| 5,073,757 A | * 12/1991 | George | 324/677 |
| 5,347,144 A | 9/1994 | Garnier et al. | |
| 5,805,049 A | 9/1998 | Yamada et al. | |
| 6,107,117 A | 8/2000 | Bao et al. | |
| 6,127,914 A | 10/2000 | Sasaki | |
| 6,193,413 B1 | 2/2001 | Lieberman | |
| 6,278,127 B1 | 8/2001 | Dodabalapur et al. | |
| 6,402,369 B1 | 6/2002 | Ludington et al. | |
| 6,436,346 B1 | 8/2002 | Doktycz et al. | |
| 6,608,323 B2 | 8/2003 | Marks et al. | |
| 6,621,099 B2 | 9/2003 | Ong et al. | |
| 6,648,503 B2 | 11/2003 | Tanaka et al. | |
| 6,742,884 B2 | 6/2004 | Wong et al. | |
| 6,770,904 B2 | 8/2004 | Ong et al. | |
| 6,774,393 B2 | 8/2004 | Murti et al. | |
| 6,803,262 B2 | 10/2004 | Wu et al. | |
| 6,843,596 B2 | 1/2005 | Verhaegen | |
| 6,855,951 B2 | 2/2005 | Ong et al. | |
| 6,861,664 B2 | 3/2005 | Ong et al. | |
| 6,872,320 B2 | 3/2005 | Wong et al. | |
| 6,890,050 B2 | 5/2005 | Ready et al. | |
| 6,890,868 B2 | 5/2005 | Wu et al. | |

(Continued)

OTHER PUBLICATIONS

"Beng Ong—Created materials for electronics that can be printed like a newspaper", Scientific American, Dec. 2004, p. 54.

(Continued)

*Primary Examiner*—Duy-Vu N Deo

(57) ABSTRACT

A passive electronic device includes layers of a layered structure on a support surface. The device can include a first layer part that includes electrically conductive or semiconductive material and that has a contact surface. The device can also include second layer parts that include electrically conductive material and are in electrical contact with the contact surface, with a subset electrically connectible to external circuitry. At least one of the parts of the two layers can be produced by a printing operation or can include a printed patterned artifact such as an uneven boundary or an alignment. The printing operation can be direct printing or printing of a mask for etching or liftoff or both. The device could, for example, be a resistive device, such as a device with resistance varying in response to non-electrical stimuli, or a conductive device, such as with a contact pad for a pogo pin.

27 Claims, 8 Drawing Sheets

U.S. PATENT DOCUMENTS

| | | |
|---|---|---|
| 6,921,679 B2 | 7/2005 | Chabinyc et al. |
| 6,972,261 B2 | 12/2005 | Wong et al. |
| 6,988,826 B2 | 1/2006 | Zribi et al. |
| 7,033,516 B2 | 4/2006 | Wong et al. |
| 7,141,210 B2 | 11/2006 | Bell et al. |
| 7,147,763 B2 | 12/2006 | Elrod et al. |
| 7,303,244 B2 | 12/2007 | Ready et al. |
| 7,473,030 B2 | 1/2009 | Bruce et al. |
| 7,473,031 B2 | 1/2009 | Wolkin et al. |
| 7,533,361 B2 | 5/2009 | Edwards |
| 7,727,768 B2 | 6/2010 | Bell et al. |
| 2003/0039585 A1 | 2/2003 | Freeman |
| 2003/0044800 A1 | 3/2003 | Connelly et al. |
| 2003/0068231 A1 | 4/2003 | Cabuz et al. |
| 2003/0134516 A1 | 7/2003 | Wong et al. |
| 2003/0160234 A1 | 8/2003 | Ong et al. |
| 2003/0164495 A1 | 9/2003 | Ong et al. |
| 2003/0186453 A1 | 10/2003 | Bell et al. |
| 2004/0195566 A1 | 10/2004 | Ong et al. |
| 2004/0196329 A1 | 10/2004 | Ready et al. |
| 2004/0201015 A1 | 10/2004 | Ong et al. |
| 2005/0017311 A1 | 1/2005 | Ong et al. |
| 2005/0040394 A1 | 2/2005 | Wu et al. |
| 2005/0129843 A1 | 6/2005 | Wu et al. |
| 2005/0133788 A1 | 6/2005 | Chabinyc et al. |
| 2005/0136358 A1 | 6/2005 | Paul et al. |
| 2005/0238080 A1 | 10/2005 | Wolkin et al. |
| 2005/0254552 A1 | 11/2005 | Bruce et al. |
| 2005/0254994 A1* | 11/2005 | Bell et al. ............ 422/51 |
| 2005/0265898 A1 | 12/2005 | Bell et al. |
| 2006/0078999 A1 | 4/2006 | Bell et al. |
| 2006/0132542 A1 | 6/2006 | Bruyker et al. |
| 2006/0158470 A1 | 7/2006 | Vanheusden et al. |
| 2006/0159585 A1 | 7/2006 | Torres et al. |
| 2006/0190917 A1 | 8/2006 | Edwards |
| 2007/0020883 A1 | 1/2007 | Arias et al. |
| 2007/0147473 A1 | 6/2007 | Wolkin et al. |
| 2007/0148416 A1 | 6/2007 | Wolkin et al. |

OTHER PUBLICATIONS

Hooge, F.N., "1/f Noise Is No Surface Effect", Physics Letters, vol. 29A, No. 3, 1969, pp. 139-140.
Office communication in U.S. Appl. No. 11/167,612, mailed Nov. 21, 2008, 36 pages.
Office communication in U.S. Appl. No. 11/318,975, mailed Oct. 15, 2008, 20 pages.
Amendment after Final Rejection in U.S. Appl. No. 11/318,975, submitted Dec. 12, 2008, 12 pages.
Office communication in U.S. Appl. No. 11/318,975, mailed Dec. 24, 2008, 3 pages.
Amendment with Request for Continued Examination in U.S. Appl. No. 11/318,975, submitted Jan. 15, 2009, 23 pages.
Office communication in U.S. Appl. No. 11/318,975, mailed Dec. 8, 2009, 24 pages.
Amendment in U.S. Appl. No. 11/167,612, submitted Dec. 9, 2009, 20 pages.
Notice of Allowance and Fee(s) Due in U.S. Appl. No. 11/149,632, mailed Dec. 29, 2009, 12 pages.
Notice of Allowance and Fee(s) Due in U.S. Appl. No. 11/149,635, mailed Jan. 4, 2010, 9 pages.
Amendment in U.S. Appl. No. 11/318,926 submitted Jan. 26, 2010, 20 pages.
Amendment in U.S. Appl. No. 11/318,975, submitted Feb. 2, 2010, 29 pages.
Amendment with Information Disclosure in U.S. Appl. No. 11/167,612, submitted Feb. 9, 2009, 11 pages.
Torres, F.E., Kuhn, P., De Bruyker, D., Bell, A.G., Wolkin, M.V., Peeters, E., Williamson, J.R., Anderson, G.B., Schmitz, G.P. Recht, M.I., Schweizer, S., Scott, L.G., Ho.
J.H., Elrod, S.A., Schultz, P.G., Lerner, R.A., Bruce, R.H., "Enthalpy arrays", Proceedings of the Nat'l Academy of Sciences, vol. 101, No. 26, Jun. 29, 2004, pp. 9517-9522.
Office communication in U.S. Appl. No. 11/318,975, mailed Mar. 6, 2009, 19 pages.
Amendment in U.S. Appl. No. 11/318,975, mailed May 27, 2009, 26 pages.
Office communication in U.S. Appl. No. 11/318,975, mailed Jul. 1, 2009, 18 pages.
Office communication in U.S. Appl. No. 11/167,612, mailed May. 26, 2009, 11 pages.
Amendment After Final Rejection in U.S. Appl. No. 11/167,612, submitted Jun. 26, 2009, 18 pages.
Office communication in U.S. Appl. No. 11/167,635, mailed Jun. 11, 2009, 38 pages.
Office communication in U.S. Appl. No. 11/167,748, mailed May 11, 2007, 24 pages.
Amendment with Information Disclosure in U.S. Appl. No. 11/167,748, dated Aug. 10, 2007, 16 pages.
Office communication in U.S. Appl. No. 11/167,748, mailed Feb. 15, 2008, 13 pages.
Amendment with Information Disclosure in U.S. Appl. No. 11/167,748, dated Apr. 15, 2008, 15 pages.
Office communication in U.S. Appl. No. 11/167,748, mailed Jun. 20, 2008, 13 pages.
Office communication in U.S. Appl. No. 11/167,746, mailed Jan. 17, 2007, 21 pages.
Amendment with Information Disclosure in U.S. Appl. No. 11/167,746, dated Apr. 17, 2007, 21 pages.
Office communication in U.S. Appl. No. 11/167,746, mailed Jul. 9, 2007, 12 pages.
Amendment after Final Rejection in U.S. Appl. No. 11/167,746, dated Sep. 7, 2007, 13 pages.
Amendment with Request for Continued Examination in U.S. Appl. No. 11/167,746, submitted Oct. 3, 2007, 12 pages.
Office communication in U.S. Appl. No. 11/167,746, mailed Dec. 28, 2007, 8 pages.
Amendment with Information Disclosure in U.S. Appl. No. 11/167,746, dated Mar. 21, 2008, 13 pages.
Office communication in U.S. Appl. No. 11/167,746, mailed Jun. 27, 2008, 7 pages.
Office communication in U.S. Appl. No. 11/318,975, mailed Apr. 29, 2008, 22 pages.
Amendment with Information Disclosure in U.S. Appl. No. 11/318,975, dated Jul. 29, 2008, 17 pages.
Amendment in U.S. Appl. No. 11/149,632, submitted Aug. 25, 2009, 24 pages.
Office communication in U.S. Appl. No. 11/167,612, mailed Jul. 15, 2009, 3 pages.
Amendment with Request for Continued Examination in U.S. Appl. No. 11/167,612, submitted Aug. 25, 2009, 21 pages.
Amendment in U.S. Appl. No. 11/167,635, submitted Aug. 25, 2009, 24 pages.
Amendment After Final Rejection in U.S. Appl. No. 11/318,975, submitted Jul. 30, 2009, 21 pages.
Office communication in U.S. Appl. No. 11/318,975, mailed Aug. 13, 2009, 7 pages.
Second Amendment After Final Rejection in U.S. Appl. No. 11/318,975, submitted Sep. 1, 2009, 21 pages.
Office communication in U.S. Appl. No. 11/318,975, mailed Sep. 16, 2009, 3 pages.
Amendment with Request for Continued Examination in U.S. Appl. No. 11/318,975, submitted Sep. 25, 2009, 27 pages.
Office communication in U.S. Appl. No. 11/318,926, mailed Oct. 30, 2009, 29 pages.
Office communication in U.S. Appl. No. 11/167,612, mailed Nov. 9, 2009, 11 pages.
Office communication in U.S. Appl. No. 11/318,926, mailed Jun. 16, 2010, 6 pages.
Amendment After Final in U.S. Appl. No. 11/318,926, submitted Jun. 3, 2010, 15 pages.
Notice of Allowance and Fee(s) Due in U.S. Appl. No. 11/167,612, mailed Mar. 31, 2010, 11 pages.
Office communication in U.S. Appl. No. 11/318,926, mailed Apr. 16, 2010, 13 pages.
Office communication in U.S. Appl. No. 11/318,975, mailed May 10, 2010, 28 pages.

* cited by examiner

FIG. 3
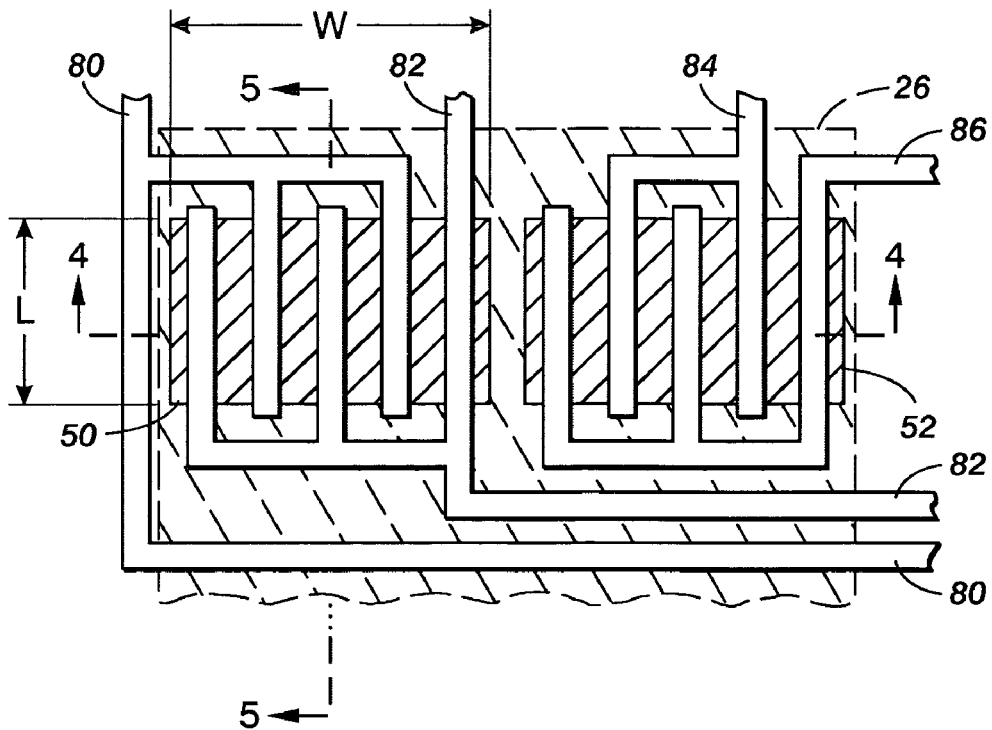
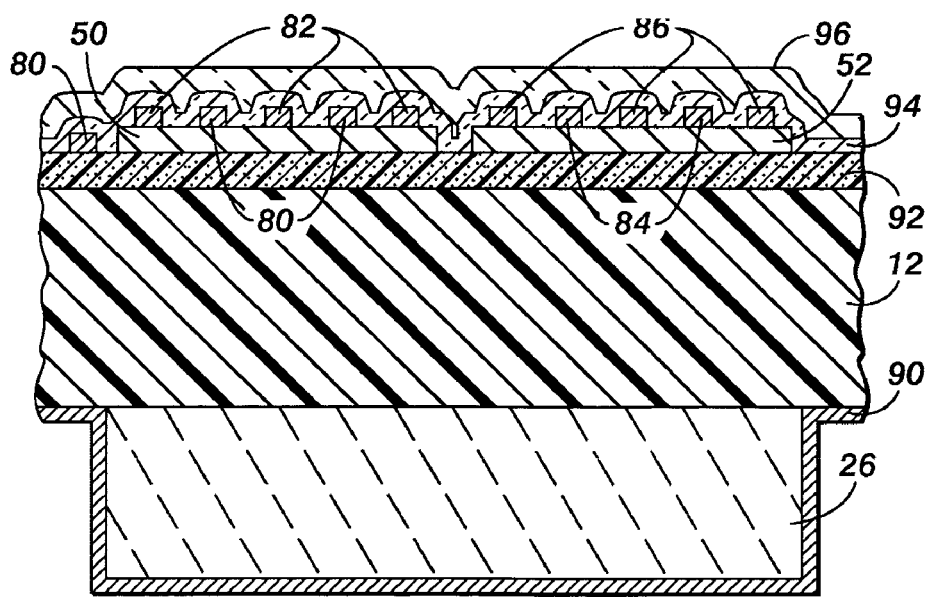
FIG. 4

PASSIVE ELECTRONIC DEVICES

CROSS-REFERENCES TO RELATED APPLICATIONS

The present application is related to the following co-pending applications, each of which is hereby incorporated by reference in its entirety: U.S. patent application Ser. No. 10/114,611 (U.S. Patent Application Publication No. 2003/0186453); "Apparatus and Method for Improved Electrostatic Drop Merging and Mixing", U.S. patent application Ser. No. 11/018,757; U.S. patent application Ser. No. 11/167,748 (U.S. Patent Application Publication No. 2005/0238080); U.S. patent application Ser. No. 11/167,612 (U.S. Patent Application Publication No. 2005/0254994); U.S. Patent application Ser. No. 11/167,746 (U.S. Patent Application Publication No. 2005/0254552); U.S. patent application Ser. No. 11/167,635 (U.S. Patent Application Publication No. 2005/0265898); "Patterned Structures Fabricated by Printing Mask Over Lift-Off Pattern", U.S. patent application Ser. No. 11/184,304; "Producing Layered Structures Using Printing", U.S. patent application Ser. No. 11/318,926; and "Layered Structures on Thin Substrates", U.S. patent application Ser. No. 11/318,975.

BACKGROUND OF THE INVENTION

The present invention relates generally to electronic devices, and more particularly to passive electronic devices.

U.S. Patent Application Publication No. 2003/0186453 describes nanocalorimeter arrays with thermal isolation regions on a substrate. A thermal isolation layer can include a plastic material in thin foil form ranging from less than 15 µm to approximately 25 µm in thickness, possibly as thin as 2 µm and as thick as 500 µm. Thermal equilibrium regions contain resistive thermometers, drop merging electrodes, and insulating layers deposited using standard fabrication techniques, such as lithographic patterning of thin films, microelectronic fabrication techniques (e.g. including sputtering, chemical etching, evaporation), and printed circuit board fabrication techniques. If amorphous silicon thermometer material is deposited, such as at temperatures in the range of 170-250° C., a substrate polymer film should have a high softening temperature. Deposition of vanadium oxide thermometer material can be done at a substantially lower temperature, allowing a substrate polymer with a lower softening point.

U.S. Patent Application Publication 2003/0134516 describes fabrication of an array of electronic devices such as a display or sensor. A droplet source ejects droplets of a masking material for deposit on a thin film or substrate surface to mask an element of an array. The droplets rapidly freeze upon contact and the thin film or substrate is then etched. A pixel of a large display system can include a thin-film transistor (TFT) or sensor or other emissive element. For example, a gate and ground plate can be formed in a first metal layer by depositing a phase change mask and then etching. A TFT's active region can be deposited, followed by a second metal layer in which a source, a data line, and a drain can be formed, again by depositing a phase change mask and etching. The drain, a dielectric, and the ground plate together can form a storage capacitor.

U.S. Patent Application Publication 2005/0136358 describes liftoff operations that involve printing liftoff patterns, such as multi-layer liftoff patterns. A mask structure may be formed from a liftoff operation, and can then be used as an etch mask, for example. The publication also describes printing of integrated circuit (IC) patterns directly on a substrate rather than using photolithography; a printed IC pattern may include gates and source and drain regions of thin film transistors, signal lines, opto-electronic device components, and so forth. Also, a patterned liftoff layer can include contact pads for an IC, electrodes for a transistor device or another structure or device, or bus lines.

It would be advantageous to have improved techniques for passive electronic devices.

SUMMARY OF THE INVENTION

The invention provides various exemplary embodiments, including devices, apparatus, arrays, and methods. In general, the embodiments are implemented with layered structures on support surfaces.

These and other features and advantages of exemplary embodiments of the invention are described below with reference to the accompanying drawings.

BRIEF DESCRIPTION OF THE DRAWINGS

FIG. 3 is a top plan view of a pair of thermistor slabs in the cell of FIG. 2.

FIG. 4 is a cross-sectional view of the thermistor slabs in FIG. 3, taken along the line 4-4.

DETAILED DESCRIPTION

Figure 1:
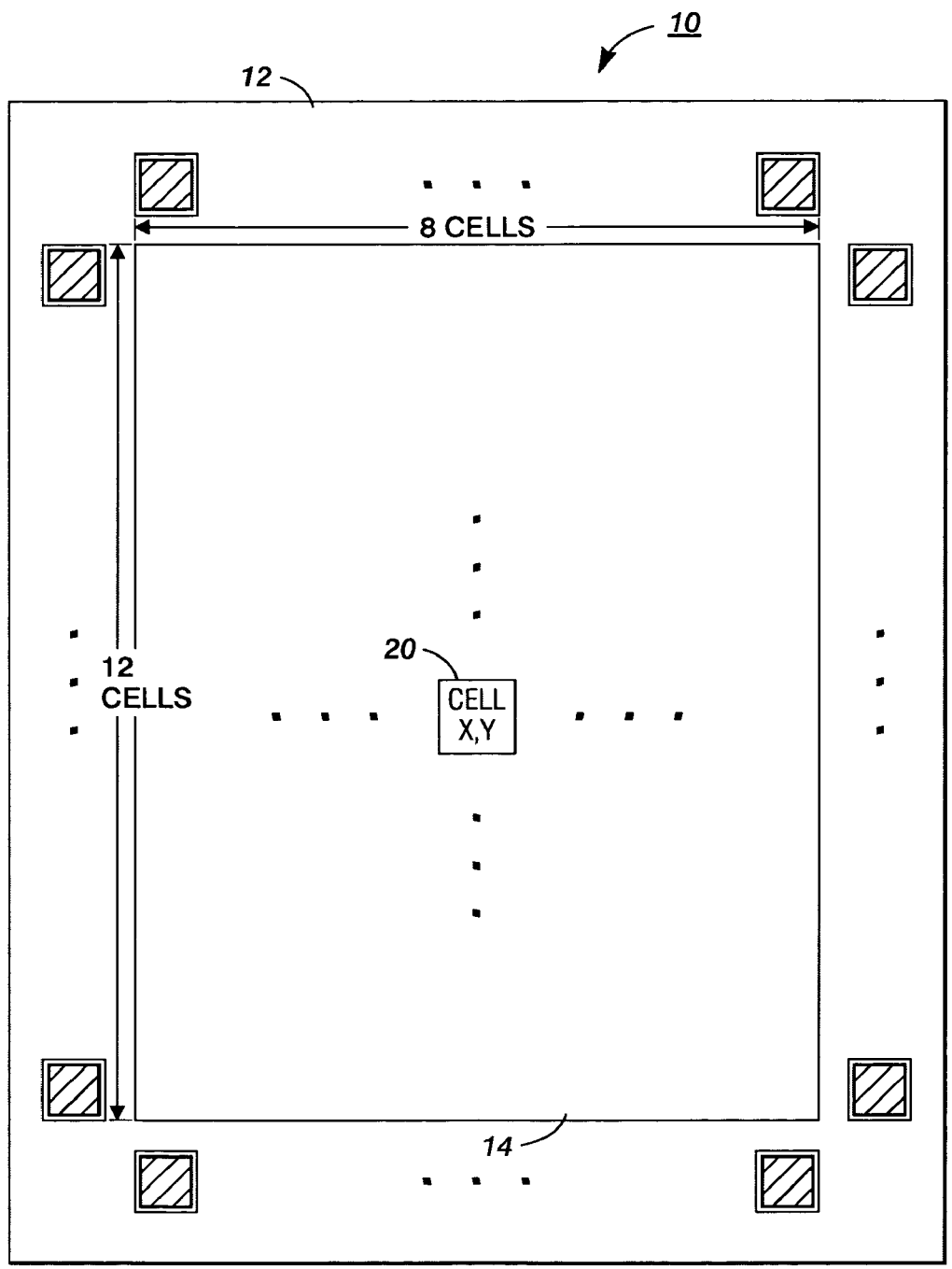
FIG. 1 is a schematic layout diagram of an integrated circuit (IC) that includes an array of thermal sensing cells on a flexible substrate.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

The implementations described below related to "electronic devices", a broad term used herein to refer generally to devices whose production or operation involves the emission, behavior, and effects of charge carriers such as electrons and holes. More specifically, some implementations described below involve "passive electronic devices" and others involve "active electronic devices". As used herein, the term "passive electronic device" refers to devices that, in operation, can transfer information electrically without gain or control; in other words, the category of passive electronic devices is complementary with the category of "active electronic devices", meaning devices that transfer information electrically with gain and/or control. Examples of passive electronic devices include resistors, conductances, capacitors, inductors, diodes (including, for example, light-emitting diodes or LEDs), and so forth. In general, transistors, on the other hand, are active electronic devices, because their operation involves gain and/or control. In addition, the category of passive electronic devices includes more complex devices that do not include any active components; for example, various filters, transducers, receivers, and transmitters can be implemented as passive electronic devices.

The exemplary implementations described below address problems that arise in electronic devices, such as in their fabrication. In particular, the implementations include calorimeters, and specifically nanocalorimeters that include 96 sensors, each able to detect temperature rises on the order of $10^{-6\circ}$ C.

One problem addressed is that of providing a low cost, high throughput tool to detect biomolecular interactions through enthalpy assay techniques; in such a tool, an informed screen would require measuring a minimum of 10,000 interactions with a small amount of material. This problem could be alleviated if enthalpy array fabrication yield and capacity could be increased while reducing cost, thus enabling a very large number of measurements. Many of the devices in a typical enthalpy array, however, are passive electronic devices, so this problem can only be alleviated with techniques that can produce such devices.

Conventional architectures for enthalpy arrays employ as many as seven different layers deposited on a thin polyimide flexible substrate such as Kapton® suspended over a cavity and laminated on its edges to a rigid metal support frame. The substrate is typically fragile, and must be stiffened to maintain good alignment and registration. In general, the substrate must be flat for accurate processing, and needs to stay in place despite heating, cooling, and other operations.

U.S. Patent Application Publication No. 2005/0238080, incorporated by reference in its entirety, describes techniques that can be implemented with a total of seven layers: Five thin layers are each deposited and photolithographically patterned on one side of the substrate, after which two thin layers are each deposited and photolithograhically patterned on the opposite side of the substrate. This approach is complicated, expensive, and unnecessarily precise because enthalpy array features have typical minimum dimensions of approximately 50 μm or greater, while photolithography can be used to produce submicron feature sizes. In one implementation, six of the seven layers have feature sizes of 50 μm or greater.

Photolithography also involves various photoresist process steps such as substrate cleaning, resist coating, soft or hard baking, mask aligning, exposing, developing, and resist dissolving, all of which may be performed for each photolithographically patterned layer, leading to many more process steps. These steps are problematic, time consuming, and apply stress and thermal budget to the flexible substrate, also possibly causing one or more layers to crack or otherwise become defective. For example, substrate cleaning can involve temperatures between 90-110° C.; resist coating can involve spinning at 1000-3000 rpm; resist baking can involve temperatures between 90-120° C.; resist aligning and exposing can involve ultraviolet illumination; resist developing can involve a wet process; and resist dissolving can involve both a dry plasma etch such as RIE and a wet process. Spinning, for example, can cause a mechanically fragile substrate to tear or become defective. Cleaning steps such as RIE followed by acetone and stronger organic solvents may lead to chemical and physical modifications of the layered structure on the substrate, such as a vanadium oxide surface; also, water rinse and air drying after each wet process can deform a thin substrate.

In addition to enduring the direct stress of photolithographic operations, the substrate must survive conflict between its plasticity and rigidity of photolithographically produced layers. For example, during heating and cooling, the substrate may expand and shrink more than the rigid layers on it, possibly causing cracking or other defects in the rigid layers. This conflict can degrade process yield and increase fabrication costs accordingly. It may also increase flicker noise, which directly correlates to lower sensor resolution.

In sum, in order to improve process yield, increase the number of functional sensors in an array, and improve resolution such as by reducing noise resulting from processing, it would be advantageous to eliminate or reduce the number of photolithographic operations used in producing an enthalpy array without compromising device performance. In addition, it would be advantageous to have techniques that can be used to produce aligned structures, whether in enthalpy arrays on flexible substrates or in any other layered structure on a support surface. And it would be advantageous to have techniques for producing passive electronic devices.

Some of the implementations described below involve thermal sensing. The term "sensing" is used herein in the most generic sense of obtaining information from a physical stimulus; sensing therefore includes actions such as detecting, measuring, and so forth. "Thermal sensing" is sensing of a thermal stimulus such as heat, temperature, or random kinetic energy of molecules, atoms, or smaller components of matter. A "thermal sensor" is accordingly an electronic device that performs thermal sensing.

A "resistive thermal sensor" is a thermal sensor with electrical resistance that varies with the thermal stimulus that it senses, in contrast to various thermal sensors that sense in other ways such as with thermocouples or thermopiles. As used herein, the term "thermistor" means an electrically resistive component that includes semiconductor material with resistance that varies in response to a thermal change; a thermistor can therefore be employed in a resistive thermal sensor. In each of these definitions, variation in electrical resistance would include both linear and non-linear variations; a non-linear variation might occur in a thermistor, for example, if a temperature change causes a phase change in the semiconductor material.

The terms "thermal signal" and "thermally conductive" or "thermally conducting", as used herein, are related. A component, layer, or other structure is "thermally conductive" or "thermally conducting" if it sufficiently conducts "thermal signals" from one position or region to another that concurrent thermally sensitive operations in the other position or region can be affected. For example, if the thermal signals include information, the information could be available for sensing and electrical detection in the other position or region. More generally, thermal signals may follow a "thermally conductive path" between two components, meaning a path along which signals are conducted.

Some of the implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes. Also, a support structure could be a "support layer", meaning a layer of material that can support other structures; for example, a support layer could include a polymer film and a barrier layer on a side of the polymer film.

As used herein, the term "thin", when applied to a substrate or other support structure, refers to a thickness that is referred to in the industry as thin. For example, a Kapton® layer of 5 mils (127 μm) thickness or less is considered thin in the industry. But 5 mil Kapton® layers are sufficiently thick that a variety of layered structures can be photolithographically produced on their surfaces and damage will be caused only infrequently.

A structure or component is "directly on" a surface when it is both over and in contact with the surface. A structure is "fabricated on" a surface when the structure was produced on or over the surface by microfabrication or similar processes. A process that produces a layer or other accumulation of material over or directly on a substrate's surface can be said to "deposit" the material. A process that etches or in some other way takes away a layer, a part of a layer, or other material from over or on a substrate's surface can be said to "remove" the material.

A "layered structure" refers herein to a structure that includes layers of material, such as microfabricated or thin film layers on a substrate or other support structure; a substrate can itself be one of the layers in a layered structure, and the substrate may in turn include layers within its structure. A "membrane", as used herein, is a sheet-like layered structure that does not itself include a rigid frame or a rigid substrate or some other rigid support structure for the layers, though a membrane can be supported by or mounted on a support structure of any suitable kind. A membrane can include a complex arrangement of structures that provide various thermally conductive paths as well as components with electrical characteristics, such as conductivity, capacitance, and resistance.

A "patterned layer" is a layer that is within a layered structure and that occurs only in one or more bounded areas of the structure. A patterned layer could be produced in many different ways, such as by depositing the layer only in bounded areas or by depositing a layer over the entire structure and then removing parts to leave bounded areas. To produce a patterned layer using photolithography is sometimes referred to herein as "patterning" the layer by photolithography or photolithographically.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. Where a sheet-like substrate or support layer has structures on two opposite surfaces, the surfaces may be arbitrarily referred to as "front side" and "back side". For a sheet-like substrate or support structure, a direction approximately parallel to one of its surfaces is "lateral". In general, it should be understood that the above directional orientation is arbitrary and only for ease of description, and that a support structure or substrate may have any appropriate orientation.

A specific microfabrication technique employed in the implementations described below is "printing", which is used herein to refer to any operation in which a fluid or fluid-like material is transferred onto one or more areas of a surface, and, after being transferred, stabilizes into a non-fluid state on substantially the same areas onto which it was transferred. Printing therefore includes any of a wide variety of techniques, including jet printing, screen printing, offset printing, photogravure, and so forth. A material that stabilizes from a fluid or fluid-like state into a non-fluid state is sometimes referred to herein as a "phase change material".

In the context of microfabrication, a "printed patterned" component is a component that is printed and that has a pattern when printing is completed. Printed patterned components can be produced in microfabrication for many purposes, including at least the following: Directly printing a printed patterned component that forms part of a microfabricated structure; printing a printed patterned component to function as a liftoff mask to pattern a subsequently deposited layer; printing a printed patterned component over a previously deposited layer to function as an etch mask for removal of exposed areas of the previously deposited layer; printing a printed patterned layer to function as an adhesive deposit mask over which an adhesive material can be deposited and the printed patterned component can then be removed to leave a pattern of adhesive material to which another material can be adhered to form a patterned layer; printing a printed patterned layer to function as a plating seed mask over which a seed material can be deposited and the printed patterned component can then be removed to leave a pattern of seed material; and so forth.

An "integrated structure" is a structure with electrical components and connections produced by microfabrication or similar processes. An integrated structure may, for example, be on or over a substrate on which it was produced or another suitable support structure. Other components could be on the same support structure with an integrated structure, such as discrete components produced by other types of processes.

Implementations of integrated structures described herein include features characterized as "cells" and "arrays", terms that are used with related meanings: An "array" is an arrangement of "cells". The term "peripheral circuitry" is used herein to refer to circuitry on the same support surface as an array but outside the array. The term "external circuitry" is more general, including not only peripheral circuitry but also any other circuitry that is outside a given cell or array.

FIG. 1 shows integrated structure 10, which includes various components integrated on fragile, flexible substrate 12, which can be a polymer layer or a silicon nitride layer, for example. Substrate 12 could include any of a variety of polymers with or without additional non-polymer layers. Candidate polymer materials include polyimide (for example, DuPont Kapton® and others), polyester (for example, DuPont Mylar®, DuPont Teonex® PEN, or DuPont Teijin® Tetoron® PET) foil, PolyEtherEtherKetone (PEEK), or PolyPhenylene Sulphide (PPS).

As shown, the components of structure 10 include array 14, an 8×12 array of 96 thermal sensing cells. To interface with standard automated laboratory equipment, the cells are positioned on 9 mm centers and the automated laboratory equipment connects with contact pads of each cell. Array 14 can be one of several arrays fabricated on a single flexible substrate.

Integrated structure 10 can, for example, be a calorimeter or nanocalorimeter array in which each cell can function as a calorimeter or nanocalorimeter. As used herein, a "nanocalorimeter" is a calorimeter capable of measuring in the range of nanocalories.

Within array 14, illustrative cell 20 is shown, within which are components that include printed patterned artifacts. As used herein, a "printed patterned artifact" is any detectable characteristic or feature of a microfabricated structure that results from production or use of a printed patterned component during microfabrication.

Printed patterned artifacts can be categorized according to how they are produced. For example, a "direct printing artifact" is an artifact that is present in a component of a structure as a result of the direct printing of the component. A "printed mask artifact", on the other hand, is a printed patterned artifact that specifically results from production or use of a printed patterned component as a mask, such as for liftoff or etching, during microfabrication. A "masked etch artifact" is a printed mask artifact resulting from use of a printed patterned component as an etch mask, while a "liftoff artifact" is a printed mask artifact resulting from use of a printed patterned component as a liftoff mask, as described for example in co-pending U.S. patent application Ser. No. 11/184,304, entitled "Patterned Structures Fabricated by Printing Mask Over Lift-Off Pattern" and incorporated herein by reference in its entirety. As discussed below, the same printed patterned component can be used both as an etch mask and as a liftoff mask, in which case both masked etch artifacts and liftoff artifacts may result from its use.

A variety of printed patterned artifacts have been detected, some of which are described below. Direct printing artifacts can, for example, include shapes of components in which print lines extend in one direction; as a result, a rectangular component, for example, may have straight boundaries or edges in one direction but scallop-like or jagged boundaries or edges in the other direction. Furthermore, all of the single lines may be of the same width, or the widths of features may all be multiples of the width of a single line, showing the use of printing techniques. In addition, all printed lines may be aligned relative to a single set of reference points as a result of a registration operation. Furthermore, the printing operation itself may leave three-dimensional printed patterned artifacts within the component. Some of these printed patterned artifacts can, in turn, result in masked etch artifacts or liftoff artifacts; in particular, the boundary and edge shapes of components, the widths of lines, and the alignment of lines and components are likely to be present in layers produced by a masked etch or a liftoff operation using a printed patterned component as a mask.

As used herein, the term "align" refers to an operation in which a feature of a structure is produced at a position by reference to another position. For example, a feature may be aligned with a position of a lower layer of a structure, or it may be aligned with alignment marks or alignment structures elsewhere in the structure, such as at the periphery.

Figure 2:
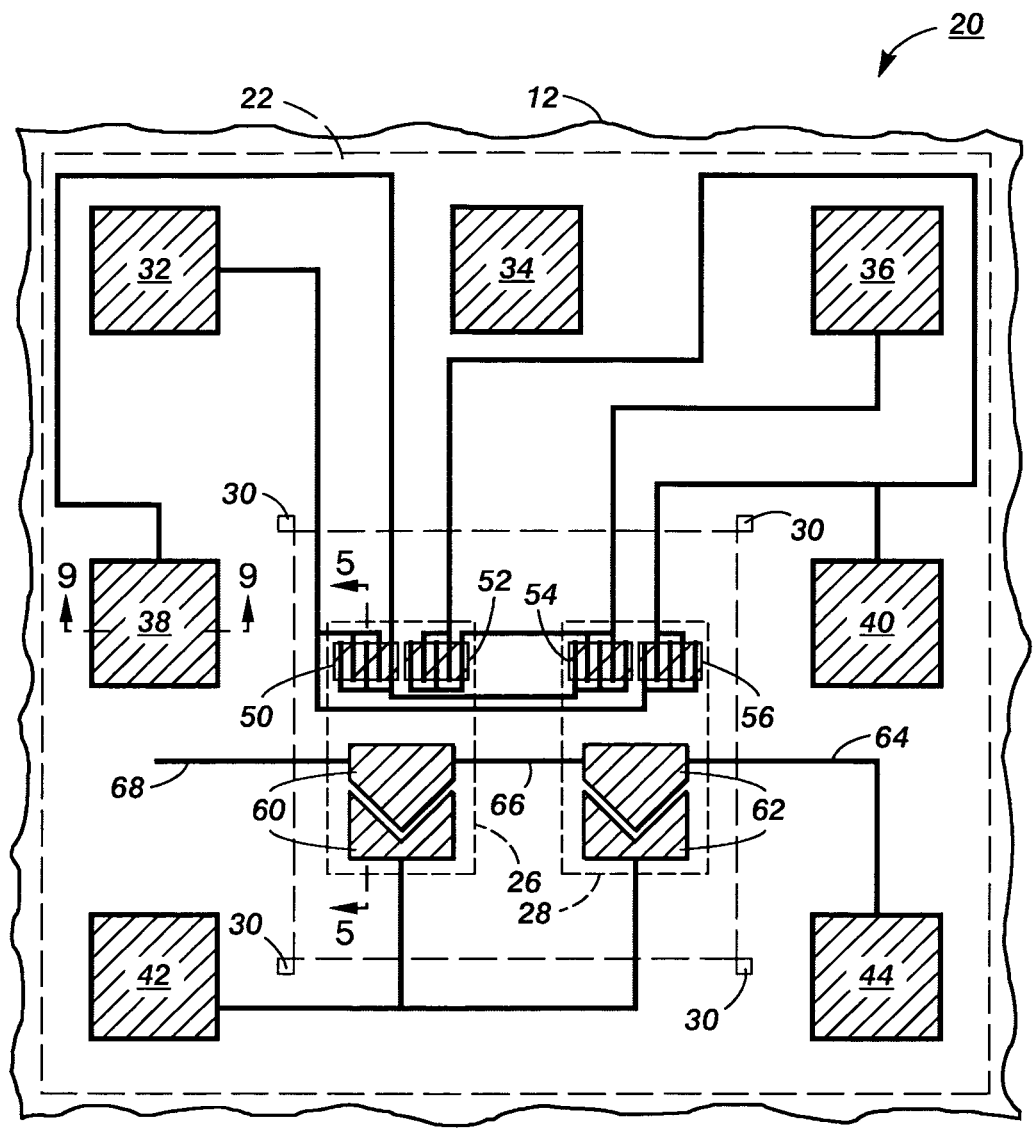
FIG. 2 is a partially schematic top view of a thermal sensing cell in the array of FIG. 1.

FIG. 2 shows an exemplary implementation of cell 20 in FIG. 1. Frame 22 (shown in dashed lines) supports substrate 12 from underneath. In addition, islands 26 and 28 (shown in dashed lines) are on the underside of substrate 12. Frame 22 illustratively has alignment structures 30 at the corners of a recess within which islands 26 and 28 are positioned. Frame 22 can, for example, be formed from 1 mm thick stainless steel in which alignment structures 30 and the recess for islands 26 and 28 are etched, and the recess can then provide thermal isolation between islands 26 and 28 as well as between either of the islands and frame 22. Thermal isolation could be maintained in various other ways.

Contact pads 32, 34, 36, 38, 40, 42, and 44 are on the upper surface of substrate 12 over frame 22. Each contact pad (except contact pad 34) is connected to one or more of the components over islands 26 and 28 by leads that are shown schematically in FIG. 2. If cell 20 is approximately square with 9 mm sides, the contact pads can be approximately 1 mm×1 mm, allowing connection with pogo pins. The leads can be approximately 50 μm wide or narrower; the leads could be even wider than 50 μm as long as they do not result in loss of thermal isolation.

Thermistor slabs 50, 52, 54, and 56 are arranged in two pairs, one including slabs 50 and 52 and the other including slabs 54 and 56. The contact pads could be connected in various ways to provide a bridge. For example, voltage VB can be applied to one of contact pads 32 and 36 while the other is connected to ground to provide a Wheatstone bridge with contact pad 38 connected to one intermediate node and with contact pad 40 connected to the other. Therefore, one of the thermistor slab pairs includes measuring thermistors while the other includes reference thermistors.

Although illustrated with thermistors as described above, cell 20 could be implemented with a variety of other resistive thermal sensors or thermal sensors of other types, such as thermocouples and thermopiles. Rather than semiconductor material, as in a thermistor, resistive thermal sensors could be made with other materials with a high temperature coefficient of resistivity (TCR) when compared with other materials. Examples of materials that have been used in resistive thermal sensors include, for example, platinum, nickel, copper, iron-nickel alloys such as balco, tungsten, iridium, oxides of nickel, manganese, iron, cobalt, copper, magnesium, and titanium, and other metals, metal alloys, and oxides of metal. Furthermore, it may be possible to produce resistive thermal sensors or other thermal sensors using other conductive or semiconductive materials.

Also, the thermistor in cell 20 is merely exemplary of a wide variety of passive electronic devices that could be implemented with the techniques described herein. An important feature of many such devices is that they can be implemented with parts in two different layers. Part of a first layer, such as a slab of electrically conductive or semiconductive material, has a contact surface, and one or more parts of a second layer of electrically conductive material are in electrical contact with the contact surface and can also be electrically connected to external circuitry, where "external circuitry" refers to circuitry outside the device. For a passive device, information must be electrically transferred without gain or control between the external circuitry and the part of the first layer through at least one of the parts of the second layer; if gain or control occurs, as occurs in a transistor for example, the device does not have the desired characteristics of a passive device.

FIG. 2 also shows drop mergers 60 and 62, on one of which a reaction can be caused so that differential temperature measurement can be performed. On the opposite side of layer 12 from drop merger 60 and slabs 50 and 52 is thermally conductive component 26. When a reaction occurs within a fluid drop under control of drop merger 60, component 26 thermally couples the drop with slabs 50 and 52, providing a thermally conductive path from the drop to thermal sensors that include slabs 50 and 52. Similarly, component 28 thermally couples a fluid drop under control of drop merger 62 with slabs 54 and 56.

Drop mergers 60 and 62 illustratively have chevron-shaped features, but could also be implemented by any of the techniques described in co-pending U.S. patent application Ser. No. 11/018,757, entitled "Apparatus and Method for Improved Electrostatic Drop Merging and Mixing", incorporated by reference herein in its entirety. Conductive line 64 extends from pad 44 to the upper part of drop merger 62, conductive line 66 extends between the upper parts of drop mergers 60 and 62, and conductive line 68 extends leftward from the upper part of drop merger 60 to provide some symmetry with conductive line 64. Pad 42 is connected to the lower parts of both drop mergers by another conductive line.

Thermistor slabs 50, 52, 54, and 56 can include semiconductor material, as described in greater detail below. Parts of the bridge circuitry, on the other hand, include conductive material such as metal or heavily doped semiconductor material; conductive components include interdigitated conductive lines that extend across and electrically contact upper surfaces of the slabs and conductive leads that connect the interdigitated lines to each other and to contact pads 32, 36, 38, and 40.

FIG. 3 shows a top plan view of thermistor slabs 50 and 52, which are similar in many respects to slabs 54 and 56. As shown, each of slabs 50 and 52 is rectangular with dimensions W and L, which are illustratively shown for slab 50, and the dimensions of slab 52 are substantially identical. Leads 80 and 82 have interdigitated lines that extend across slab 50, while leads 84 and 86 have interdigitated lines that extend across slab 52.

FIG. 4 shows slabs 50 and 52 in cross section along the line 4-4 in FIG. 3. Substrate 12 can, for example, be a 3 mil (76.2 µm), 2 mil (50.8 µm), 1 mil (25.4 µm), or ½ mil (12.7 µm) thick polyimide layer such as Kapton® film from DuPont, on which other components are microfabricated in a manner described in greater detail below. Substrate 12 provides thermal isolation between slabs 50 and 52 and other components and, for this purpose, any other suitable thermally isolating film could be used instead of polymer, including inorganic materials, such as silicon nitride (SiN).

Thermally conductive component 26 is on the lower surface of polymer layer 12, and can include thermally conductive metal such as copper or aluminum at a thickness of 9 µm or thinner; in general, component 26 can include any thermally conductive material and desired conduction can be obtained by adjusting thickness in proportion to the material's thermal conductivity.

Deposited over thermally conductive component 26 is anti-coupling layer 90, which could be implemented as a 10 nm thick layer of gold, and functions to prevent capacitive coupling between adjacent parts of thermally conductive component 26. Because it is very thin, layer 90 has low thermal conductivity, preserving thermal isolation. Implementations of layer 90 and of other applicable anti-coupling measures are described in greater detail in co-pending U.S. patent application Ser. No. 11/167,746, entitled "Thermal Sensing", and incorporated herein by reference in its entirety.

On the upper side of substrate 12, barrier layer 92 protects against contaminants and humidity, increasing device performance; barrier layer 92 has been successfully implemented with a layer of approximately 300 nm of silicon oxynitride ($SiO_xN_y$). Slabs 50 and 52 are on barrier layer 92, and include material making it possible for the thermistor pair to be low noise thermistors. Leads 80, 82, 84, and 86 are on the upper surfaces of and in electrical contact with slabs 50 and 52 and, in places, on barrier layer 92. Leads 80, 82, 84, and 86 can be implemented, for example, with a suitable conductive metal sandwich such as Cr/Al/Cr or TiW/Al/Cr to provide electrical contact with slabs 50 and 52 and to provide conductive paths to other circuitry, i.e. to external circuitry.

Additional layers deposited over leads 80, 82, 84, and 86 provide electrical passivation, environmental barriers, and hydrophobic surfaces, which are especially useful for a system in which temperatures of reactions between fluids are measured through drop deposition and merging. In FIG. 4, these layers illustratively include protective layer 94 and polymer layer 96. Protective layer 94 can be produced by plasma-enhanced chemical vapor deposition (PECVD) of silicon oxynitride, silicon oxide, or silicon nitride, such as to a thickness of approximately 300 nm, while polymer layer 96 can include a layer of parylene deposited to a thickness of approximately 2 µm, to provide a barrier to liquid and to leakage and to provide some hydrophobicity. Fluorocarbon polymer can be dip-coated over the parylene to obtain a more hydrophobic surface. Alternatively, polymer layer 96 could include a Teflon® coating from DuPont or a similar material.

Figure 5:
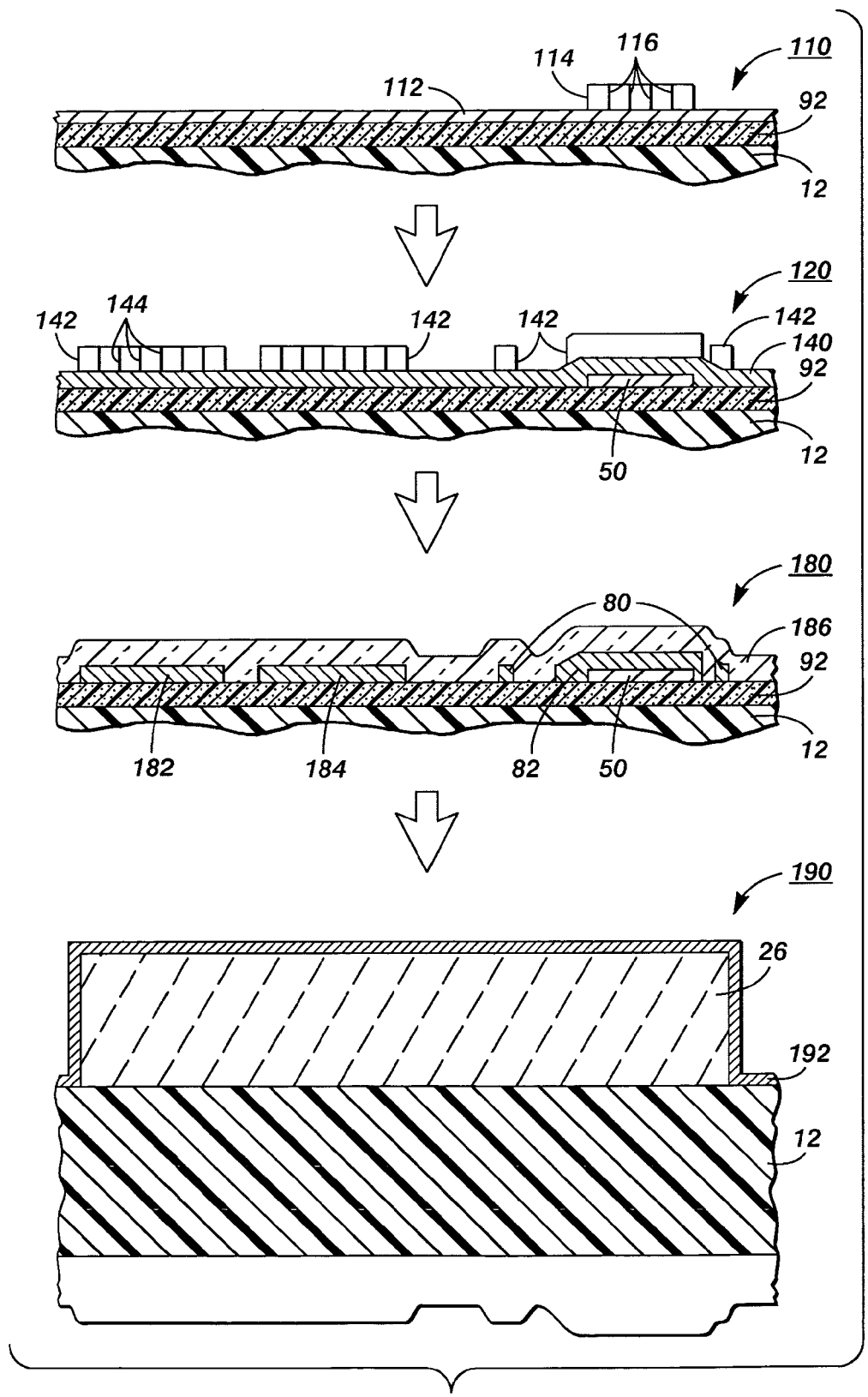
FIG. 5 is a sequence of cross-sectional views of the cell of FIG. 2, taken along the lines 5-5 in FIGS. 2 and 3 and showing stages in producing the cell.

FIG. 5 shows several cross sections in producing cell 20 as in FIGS. 2-4, taken along line 5-5 in FIGS. 2 and 3. As can be seen from FIG. 3, line 5-5 extends through the middle digit of lead 82 where it extends over slab 50.

Prior to cross section 110 in FIG. 5, substrate 12 is prepared for subsequent operations. As noted above, substrate 12 can be a 3 mil (76.2 µm), 2 mil (50.8 µm), 1 mil (25.4 µm), or ½ mil (12.7 µm) thick Kapton® film or other polyimide film and is generally held flat during processing, because flatness is important for printing and photolithography and for uniform feature sizes. Prior to deposition of material on substrate 12, the surfaces of substrate 12 are cleaned, and substrate 12 is stretched and mounted by lamination on a frame (not shown). Mounting substrate 12 on a stainless steel frame reduces the risk of curling or cracking during processing, especially if substrate 12 is not laminated.

Cross section 110 shows a portion of substrate 12 on which barrier layer 92 has been deposited. Barrier layer 92 has been successfully implemented with PECVD silicon oxynitride deposited to a thickness of 300 nm, which has been successful in producing a low noise thermistor. Other materials may also be suitable, including insulating films such as sputtered silicon oxide or PECVD silicon oxide or oxynitride, where "silicon oxide" and "silicon oxynitride" include any possible stoichiometry of silicon with oxygen or silicon with oxygen and nitrogen, respectively; for example, silicon oxides could also be referred to as $SiO_x$, and include SiO, $SiO_2$, and so forth. When properly deposited, barrier layer 92 provides improved surface smoothness and a humidity and contamination barrier.

Cross section 110 also shows layer 112 with semiconductor thermistor material deposited over barrier layer 92. Layer 112 could include vanadium oxide ($VO_x$), heavily p-doped amorphous silicon, or other materials suitable for low noise thermistors. Unless otherwise specified, the terms "vanadium oxide" and "$VO_x$" refer herein to any oxide or combination of oxides of vanadium that can be used in the context, such as $V_2O_5$, $VO_2$, $V_2O_3$, VO, and so forth. In addition to vanadium oxide and amorphous silicon, as mentioned above, other semiconductor materials with high TCR that would be candidates for use in layer 112 include yttrium barium copper oxide (YBCO) and mercury cadmium telluride.

Layer 112 has been successfully implemented by sputtering $VO_x$ over barrier layer 92 under deposition conditions that obtain required electrical and thermal characteristics and low compressive stress to prevent deformation and provide flatness in layer 112. The thermistor material in layer 112 plays a key role in detector sensitivity. Sensitivity is directly correlated with TCR and inversely proportional to a detector's noise.

In a specific experimental example, a $VO_x$ film was DC sputtered onto a glass substrate using a vanadium target in a mixed oxygen/argon environment. The sputtering conditions were optimized to yield a highly thermally sensitive and low noise film with typical sheet resistance of 500 kΩ/square and TCR of 3.4%.

After layer 112 has been deposited, an annealing operation improves low noise characteristics. In particular, annealing in an appropriate gas such as $N_2$ at a suitable temperature for an appropriate period of time decreases resistivity of layer 112 and reduces 1/f noise level of a resulting thermistor. Sheet resistance values on the order of 400 kΩ/square have been obtained for 300 nm thick film of $VO_x$, and values in a wide range of resistivities, approximately 300-800 kΩ/square, have been achieved for $VO_x$ with high TCR and low 1/f noise.

It should be noted that the device resistance of thermistors in cell 20 plays an important role in sensitivity. In general, high resistance increases Johnson noise, while low resistance causes poor offset matching and raises issues with interconnect line resistance and pogo pin contact resistance. The arrangement of interdigitated fingers, illustrated in FIGS. 2-4, provides an elegant solution to this problem. It has been shown that four folded fingers with a total area of 24 square reduce device resistance to approximately 12 kΩ, with about 8 μK of Johnson noise and with optimization for signal analysis. Higher or lower device resistances would degrade sensitivity. Folding of the fingers is also important in reducing the dimensions of cell 20, which helps to reduce thermal signal delay between drop mergers and thermistors.

Additional information about techniques for producing layer 112 and about its characteristics and characteristics of other semiconductor layers for low noise sensors is set forth in co-pending U.S. patent application Ser. No. 11/167,748, entitled "Resistive Thermal Sensing", and incorporated herein by reference in its entirety.

Cross section 110 also illustrates wax feature 114 jet printed over layer 112 to serve as an etch mask. As can be seen, wax feature 114 is a printed patterned component that includes artifacts of printing, schematically represented by darkened areas 116, each of which represents a boundary between printed lines. The size of lines within wax feature 114 can be controlled by adjusting the surface energy and substrate temperature during the jet printing process.

Although feature 114 and various other features described herein are referred to as "wax", that word is not intended to indicate chemical composition, but rather characteristics of the material when printed. More specifically, in contrast to inks, toners, and other materials that can be printed, "wax" refers to a material that changes phase during or shortly after being transferred onto a medium, changing from fluid or fluid-like form to solid or semi-solid form. Examples of such materials are described, for example, in U.S. Pat. No. 6,972,261, incorporated herein by reference in its entirety.

Although not explicitly shown, the printing of feature 114 and all other printed features described herein includes an aligning operation by which each printed line is positioned relative to one or more alignment marks or structures. Alignment structure 30 (FIG. 2) could be used for this purpose, for example.

Cross section 120 shows a stage after cross section 110, in which etching has been performed to remove areas of layer 112 except those covered by the etch mask that includes wax feature 114. Specifically, thermistor slab 50 remains after the etching of layer 112. Any suitable technique could be used to perform etching, including wet or dry etching. As a result of production with printed wax feature 114, slab 50 includes printed patterned artifacts, some of which may be seen in FIG. 6.

Figure 6:
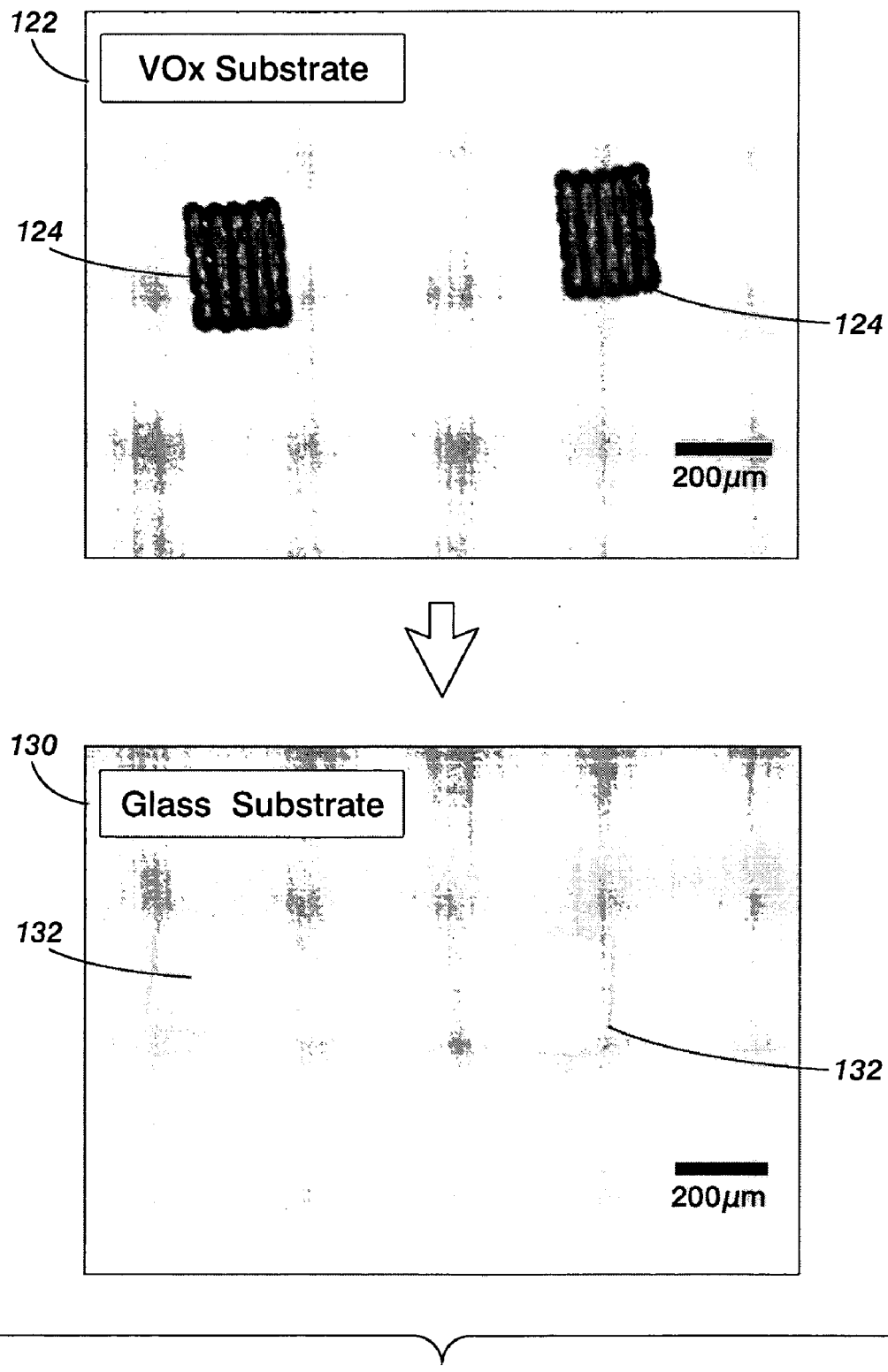
FIG. 6 shows a sequence of images from an experimental example that produced slabs of semiconductor material with printed patterned artifacts.

FIG. 6 shows subsequent steps in the experimental example described above, in which $VO_x$ was sputtered on a glass substrate. Image 122 in the upper part of FIG. 6 shows wax features 124, printed patterned components that are jet printed over the sputtered $VO_x$ film to function as etch masks. Each of wax features 124 includes five adjacent printed lines, and the boundary regions between adjacent lines as well as scallop-like shapes at the ends of the lines are examples of artifacts of printing. In the illustrated experiment, the temperature of the substrate was maintained at 40° C. during printing and 40 μm line widths were obtained. After wax features 124 were printed, the $VO_x$ film was etched using a reactive ion etch (RIE) under an oxygen and $CF_4$ environment with the thermistor slabs well protected by wax features 124.

Image 130 in the lower part of FIG. 6 illustrates the appearance of thermistor slabs 132 after etching and after removal of wax features 124 using a THF solution which removed the wax easily in a single step. As may be visible in image 130, each of slabs 132 includes printed patterned artifacts, such as scalloped edges similar to those of wax features 124.

Advantages of printing an etch mask to produce thermistor slabs as illustrated in FIG. 6 include the simplicity of the process and the reduction of the number of process steps. In contrast to a typical photoresist etch mask, wax features 124 were easily dissolved from the $VO_x$ surface, eliminating the need for further cleaning using plasma and organic solvents as are typically required with a photoresist mask. The use of plasma and organic solvents is problematic because it may result in surface modification and degradation of contact with the next layer deposited over slabs 132.

Cross section 120 in FIG. 5 also illustrates conductive layer 140, which can be produced by depositing a metal stack such as Cr/Al/Cr or TiW/Al/Cr. If slab 50 includes $VO_x$, TiW/Al/Cr may provide better ohmic contact with slab 50, improving noise performance. Cross section 120 also shows wax features 142 printed over layer 140 to provide another etch mask, with a 50 μm line width as suggested by shading 144 to illustrate artifacts of printing. After printing of wax features 142, a wet etch can be performed to produce electrodes of drop merger 60 (FIG. 2) and leads 80 and 82.

In an alternative technique to that shown in FIG. 5, wax features complementary to the mask that includes wax features 142 can be printed over the structure shown in cross section 120 prior to the deposition of layer 140. Then, after layer 140 has been deposited, a liftoff operation can be performed to remove material over the wax features, leaving other portions of layer 140 intact.

Figure 7:
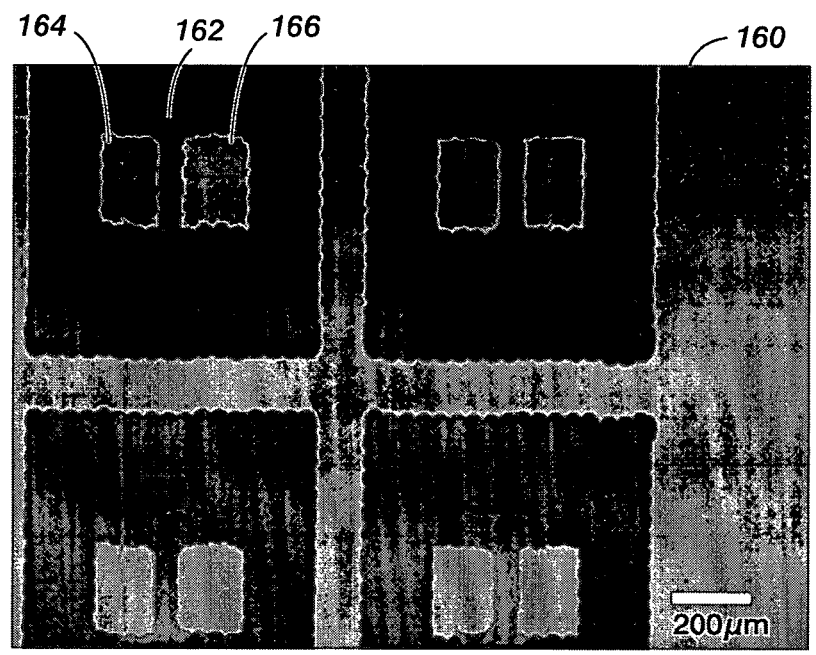
FIG. 7 shows an image from another experimental example in which slabs of semiconductor material similar to those in FIG. 6 are partially covered by conductive material to produce a thermistor-like structure.

FIG. 7 shows an image 160 of another experimental example performed on a glass substrate. Image 160 shows portions of four regions in which operations have been concurrently performed to produce similar thermistor-like structures.

In the region in the upper left portion of image 160, $VO_x$ slab 162 is partially covered by electrodes 164 and 166. Electrodes 164 and 166 were produced similarly to the alternative technique described above: A liftoff mask was printed over slab 162, producing a printed patterned component. A metal stack with layers of chromium and gold was then deposited by DC sputtering to produce a conductive layer similar to layer 140 in cross section 120 in FIG. 5. The conductive layer was then patterned by lifting off the mask in a vibrating THF solution, which easily removed the mask and the overlying metal. The remaining portions of the conductive layer included printed patterned artifacts, as can be seen in FIG. 7.

Figure 8:
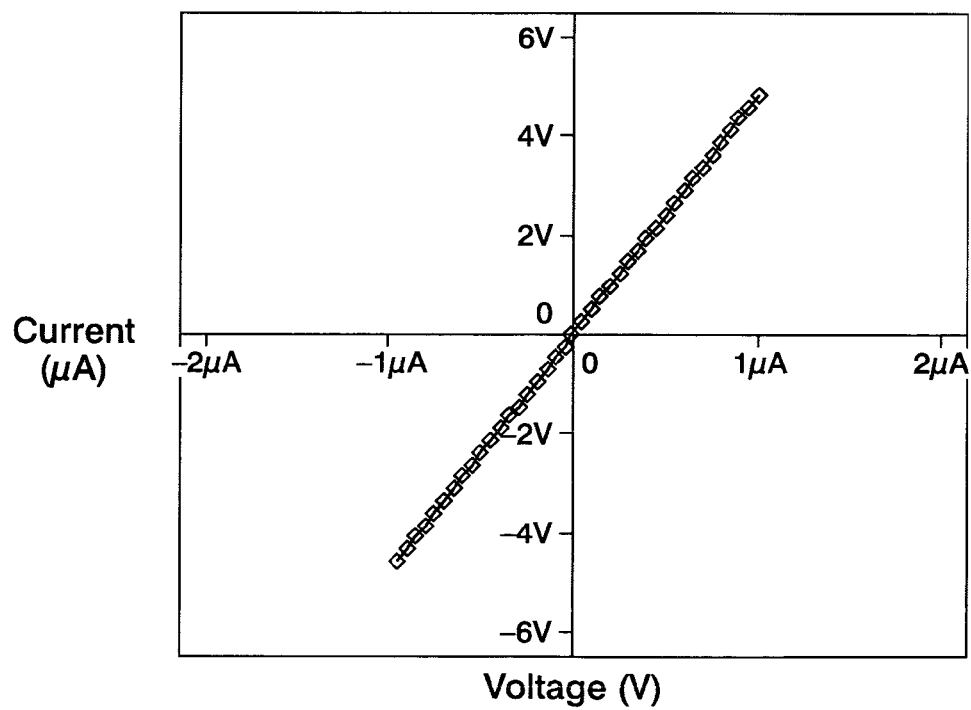
FIG. 8 is a graph showing measured current as a function of applied voltage for a thermistor-like structure as in FIG. 7.

FIG. 8 is a graph showing the current/voltage characteristic of a thermistor-like structure as shown in FIG. 7. Because measured current is a linear function of applied voltage, FIG. 8 demonstrates that ohmic contacts were produced between electrodes 164 and 166 and slab 162. Therefore, the use of a printed liftoff mask did not damage the electrical properties of the materials.

The experiment illustrated in FIGS. 7 and 8 shows that ohmic contact required for linear signal processing can be established with, for example, a Cr/Al/Cr composite layer deposited over a printed wax mask which is then lifted off to produce metal stack electrodes, leads, and lines with 50 μm line width. In an alternative architecture, a composite metal stack of Cr/Al/TiW would be deposited and then a mask would be printed over it, with the metal stack being patterned by wet etching prior to deposition of a $VO_x$ film. With either implementation, it would be important to use interdigitated fingers rather than electrodes shaped as in FIG. 7, for the reasons set forth above.

The technique demonstrated by the experimental example of FIGS. 7 and 8 is advantageous because it reduces the number of processing steps and simplifies the liftoff process. The use of printing for patterning a conductive metal layer on flexible substrates is advantageous compared to conventional photolithography in which the liftoff process is long, aggressive, and can result in film delamination, which did not occur with the experimental example. Printing reduces the number of elevated temperature processes (such as photoresist bake) that can cause flex deformations and defects in the noncompliant rigid layers on top. The number of processing steps is also reduced when printing is used, further reducing substrate deformation caused by solvent absorption and solvent incompatibility.

Electrodes, leads, and lines produced by liftoff or wet etch techniques will include printed patterned artifacts, some of which are visible in FIG. 7. For example, electrodes 164 and 166 show scallop-like ends resulting from the printing of the mask layer. It would also be possible to produce electrodes, leads, and lines by direct printing, in which case additional printed patterned artifacts would arise. For example, a number of solution processed conducting materials such as metal nanoparticles or conjugated polymers can be deposited by jet printing. With the direct printing approach, deposition and patterning occur at the same time in a single processing step.

Cross section 180 in FIG. 5 shows a subsequent stage at which conductive layer 140 has been patterned by one of the techniques described above. As a result, leads 80 and 82 extend across slab 50 as well as around it, while electrodes 182 and 184 of drop merger 60 are also produced. Other electrodes, leads, and lines shown in FIG. 2 are also produced in this stage, as well as the contact pads, all of which include conductive material from layer 140.

Cross section 180 also shows top layer 186, which can be produced by depositing protective layer 94 and polymer layer 96 (FIG. 4). As described above, layers 94 and 96 provide an upper barrier layer, and openings can be etched through layers 94 and 96 in the manner described below in relation to production of contact pads.

After production of contact pads, the layered structure on one surface of substrate 12 can be completed, such as by depositing and patterning a coating of parylene. Cross section 190 in FIG. 5 shows a structure produced on the other side of substrate 12, including thermally conductive component 26. In one approach, component 26 could be produced by depositing a 9 μm layer of copper and by then printing a wax mask over it, with only the areas outside component 26 exposed. The mask pattern could be aligned with the layered structure on the opposite surface of substrate 12 using any suitable technique, such as an alignment mark or structure that extends through substrate 12. Then, exposed copper areas could be removed by any suitable etching process.

This example illustrates a major advantage of jet printing in production of layered structures on flexible substrates. Due to processing temperatures, flexible substrates deform, and the alignment of a deformed substrate to a hard mask is extremely difficult. With jet printing, the mask is a digital pattern, so that registration can be obtained by correcting the alignment for changes in the substrate. Jet printing could also be used in conjunction with conventional photolithography, in which case a complete structure would be produced by a form of hybrid patterning, where some layers are patterned by wax printing and others that need smaller feature resolution are patterned by photolithography.

In one implementation, the starting substrate can be a premanufactured structure that includes substrate 12, a polymer layer, on which a layer of copper has been electrodeposited. The copper could be produced, for example, by depositing one or more thin seed layer such as a chromium seed layer and a copper seed layer and then electroplating copper onto the seed layers. Techniques for producing such a starting substrate are described in U.S. Pat. No. 4,863,808, incorporated herein by reference.

Cross section 190 also illustrates anti-coupling coating 192 deposited over component 26. After deposition of coating 192, the resulting structure can be cut off of the frame on which it was mounted during processing and can be attached to frame 22 (FIG. 2). Frame 22 acts as a stiffener to hold substrate 12 taut and flat. Further operations can be performed, such as laser trimming of slabs to balance ridges.

When connected in a bridge circuit, cell 20 can be operated as follows: Two drops of approximately 250 nl can be released on each of drop mergers 60 and 62. The drops on one merger can initiate a reaction such as a protein-ligand binding reaction, an enzymatic reaction, or an organelle activity, while the drops on the other merger can be non-reactive, providing a reference for differential measurement. After the drops reach thermal equilibrium, the drops on both mergers can be concurrently merged and mixed by applying appropriate voltage signals across drop merger electrodes (e.g. electrodes 182 and 184 in FIG. 5).

A thermal input signal resulting from merging and mixing of drops is conducted downward through the layered structure and part of substrate 12 to thermally conductive component 26 or 28. Then the thermal input signal is conducted laterally to a region under slabs 50 and 52 or slabs 54 and 56 where the signal is conducted upward to the slabs through substrate 12 and layer 92. A change in temperature in the slabs on one side of cell 20 changes their resistance, resulting in detection of a current through a Wheatstone bridge circuit that would be balanced if resistance were the same as that of the reference thermistors on the other side of cell 20. The current's magnitude indicates the temperature difference between the measuring thermistors and the reference thermistors.

Figure 9:
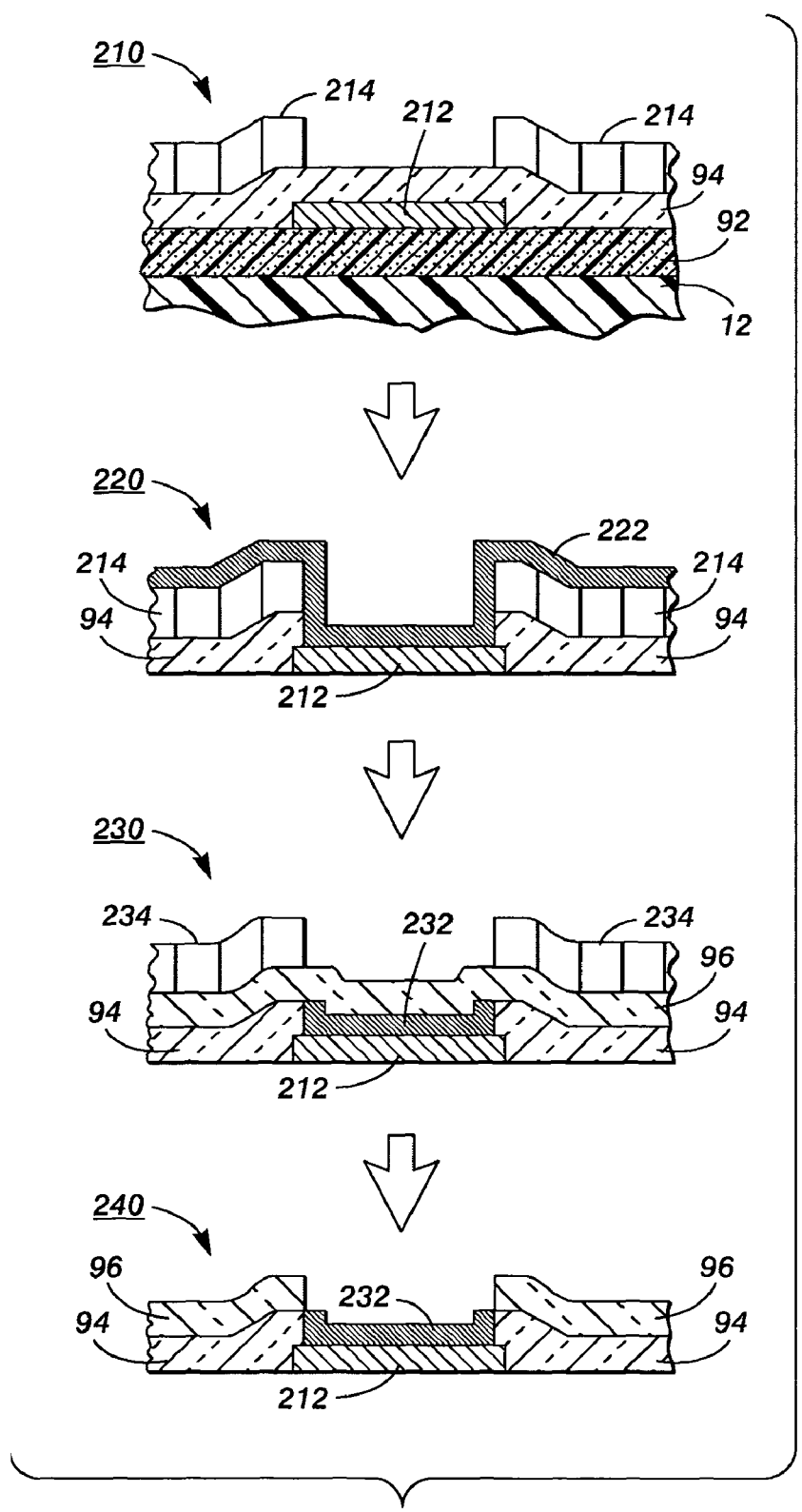
FIG. 9 is a sequence of cross-sectional views of the cell of FIG. 2, taken along the line 9-9 and showing stages in producing a contact pad.

FIG. 9 shows several cross sections in producing contact pad 38 in FIG. 2, taken along line 9-9. Due to its internal structure, contact pad 38 can also be treated as a passive electronic device, characterized as a conductance. The illustrated cross sections illustrate in more detail how any of contact pads 32, 34, 36, 38, 40, 42, and 44 in FIG. 2 can be produced by operations performed between cross sections 120 and 180 in FIG. 5.

Cross section 210 in FIG. 9 illustrates a stage in which pad body 212 has been produced in the patterning of conductive layer 140. Then, protective layer 94 is deposited, such as by PECVD of silicon oxynitride, providing a moisture and contamination barrier over cell 20. In order to provide good contact with pad body 212, however, protective layer 94 must be etched over pad body 212. Therefore, wax mask 214 has been printed over protective layer 94 with an opening over pad body 212. The opening can, for example, be a square with 1500 μm on a side.

Cross section 220 shows a subsequent stage in processing in which etching has been performed to remove the silicon oxynitride of layer 94 from over pad body 212. Then, to provide improved electrical contact, such as with pogo pins, highly conductive layer 222 has been deposited, such as by first sputtering a 40 nm adhesion layer of titanium and by then sputtering a 80 nm layer of gold over it. Note that layer 222 covers the exposed portion of pad body 212 as well as mask 214.

Cross section 230 shows a subsequent stage in which a liftoff operation has been performed to remove mask 214 and the portion of layer 222 over mask 214, leaving contact 232 on pad body 212. This operation could be performed in a vibrating THF solution, in the manner described above in relation to FIG. 15. Then, protective layer 96 has been deposited over protective layer 94 and contact 232. As noted above, layer 96 can be parylene to provide an additional barrier layer and a hydrophobic base for proper operation of drop mergers. Finally, etch mask 234 has been printed over protective layer 96.

Finally, cross section 240 shows the result of a further etching operation to remove protective layer 96 over gold contact 32, leaving a "contact via", meaning an opening through which electrical contact can be made, such as with a pogo pin. This can be done by etching the parylene in layer 96 using an RIE etch. Note that mask 234 can have exactly the same pattern as mask 214, simplifying the processing, and can be similarly removed after etching has been performed. As a result of these operations, pad body 212 has good ohmic contact with pogo pins through gold contact 232, which is therefore electrically connectible to external circuitry. During operation of contact pad 38, information is electrically transferred without gain or control between external circuitry and pad body 212 through gold contact 232.

Figure 10:
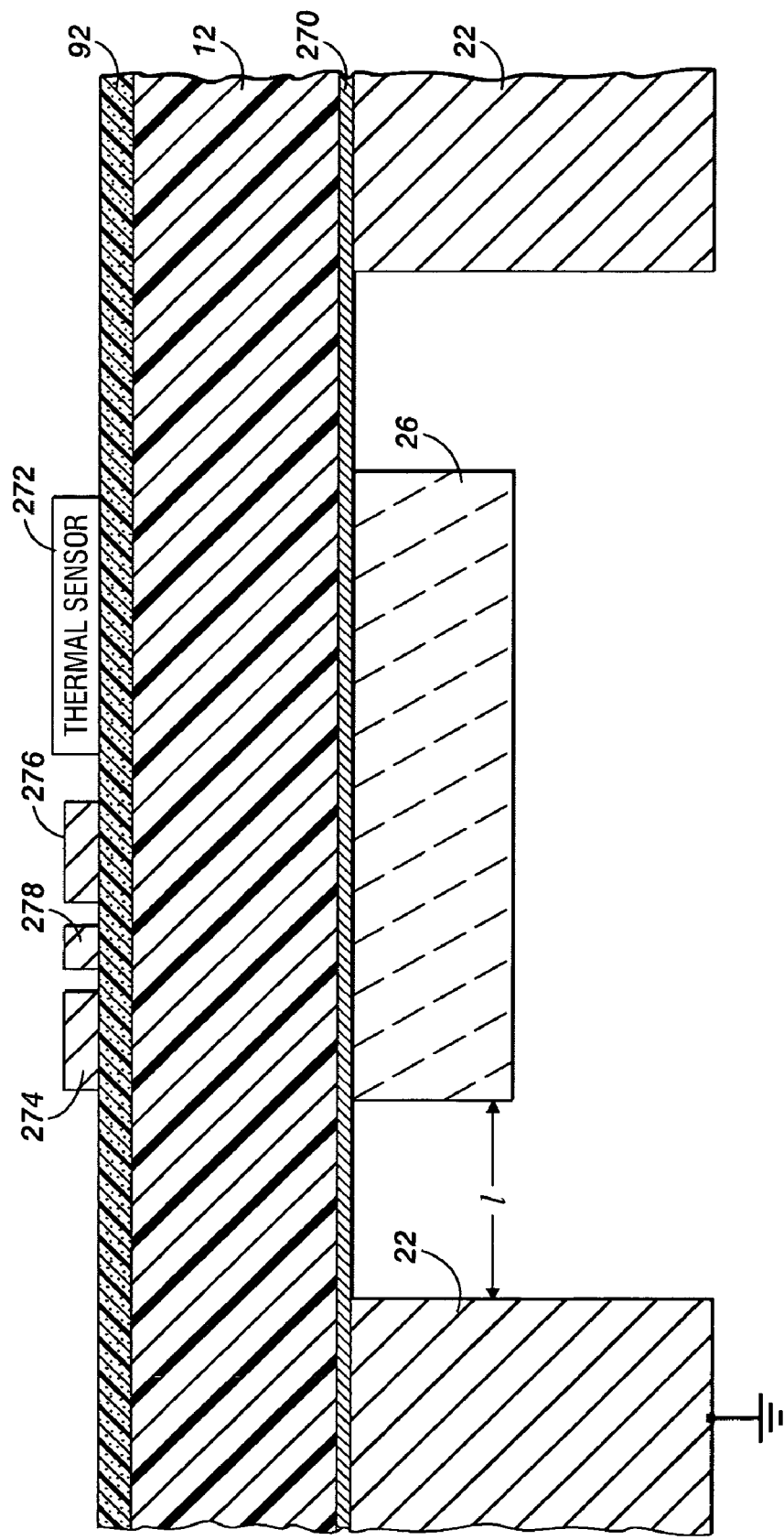
FIG. 10 is a cross-sectional view of an alternative implementation of a thermal sensing cell that can be used in the array of FIG. 1.

After completion of structures on substrate 12, as described above, and after mounting on a stainless steel frame, a cross section similar to that in FIG. 10 results, although some of the features shown in FIG. 10 are different than those described above, illustrating alternative implementations. In particular, FIG. 10 illustrates frame 22, a conductive material connected to ground so that an anti-coupling layer can be grounded. The anti-coupling layer could be over component 26 as shown in cross section 190 in FIG. 5, or, as shown in FIG. 10, could be under component 26, as illustrated by layer 270. Frame 22 can also provide a thermally stable support for the multi-layered structure that includes substrate 12. Frame 22 can have a high thermal inertia.

The combination of component 26 and layer 270 can be fabricated by beginning with a multi-layer film that includes a polymer layer, i.e. substrate 12, a chromium layer that will become layer 270, and a copper layer from which component 26 can be produced by etching in an appropriate pattern. As described above, the etching operation could be performed through a printed etch mask (not shown), and the etchant must remove the material in the exposed copper layer while leaving exposed chromium in layer 270 for conduction. Other techniques for production of or mounting on frame 22 are described in co-pending U.S. patent application Ser. No. 11/167,746, entitled "Thermal Sensing", and incorporated herein by reference.

FIG. 10 also illustrates thermal sensor 272, shown schematically, as well as electrodes 274, 276, and 278. Thermal sensor 272 could be implemented with a semiconductor structure such as slab 50 in FIG. 5, with conductive lines extending across an upper or lower contact surface or with other suitable components. Electrodes 274, 276, and 278 provide an alternative implementation to the chevron-shaped drop mergers illustrated in FIGS. 2 and 5.

In a current implementation, electrode 278 is electrically connected to ground through a contact pad, while electrodes 274 and 276 are driven by time-varying signals at an appropriate voltage such as 120 volts or greater, also provided through one or two contact pads. In a current implementation, these signals include pulses of approximately 50 msec and 120 V amplitude with rise times in the range 1-50 μsec.

The implementations in FIGS. 1-10 illustrate examples of passive electrical devices that include part of a first layer with a contact surface and, in electrical contact with the contact surface, parts of a second layer. The first layer includes electrically conductive or semiconductive material, while the second layer includes electrically conductive material. A subset of the second layer's parts are electrically connectible to external circuitry. The layers are within a layered structure on a support surface, and at least one of the parts includes one or more printed patterned artifacts. In operation, information is electrically transferred without gain or control between the external circuitry and the part of the first layer through at least one of the subset of the second layer's parts.

In specific implementations, the first layer can include resistive semiconductive material and the second layer can include electrically conductive metal; or both layers can include electrically conductive metal. The external circuitry can include a contact pad within the layered structure, and one of the subset of the second layer's parts can be electrically connected to the contact pad. Or, the external circuitry can include a pogo pin external to the layered structure, with the subset of the second layer's parts including a contact pad that can be electrically contacted by the pogo pin. The printed patterned layer artifacts can include at least one of liftoff artifacts, masked etch artifacts, and direct printing artifacts. For example, they can include an uneven boundary portion or alignment with a position of a lower layer or with an alignment mark or alignment structure.

In one specific implementation, the device is a resistive device, with the part of the first layer a resistive component. The subset of the second layer's parts includes first and second leads in electrical contact with the resistive component at first and second areas of the contact surface that are spaced apart. The resistance between the first and second leads can, for example, vary in response to non-electrical stimuli. The electrically transferred information can indicate detection of the non-electrical stimuli.

In another specific implementation, the device is a conductive device, with the part of the first layer a conductive component. The subset of the second layer's parts can include a metal contact pad in electrical contact with the conductive component over substantially the entire contact surface. The first layer can include a stack of conductive metal sublayers, while the second layer can include an adhesion sublayer on the contact surface and a gold sublayer on the adhesion sublayer.

The implementations in FIGS. 1-10 also illustrate examples of passive electronic devices that include part of a resistive first layer with a contact surface and, in electrical contact with the contact surface, first and second parts of a second layer. The first layer includes semiconductive material, while the second layer includes electrically conductive material. The second layer's first and second parts each include a respective set of parallel lines extending across and in electrical contact with the contact surface and a connecting part not in contact with the contact surface but that electrically connects the set of lines. The sets of lines are interdigitated. As above, the layers are within a layered structure and information is electrically transferred without gain or control. Each of the parts includes one or more printed patterned artifacts.

In specific implementations, the resistance between the second layer's first and second parts can vary in response to non-electrical stimuli, allowing electrical detection of the non-electrical stimuli by circuitry connected across the first and second parts. The first and second parts can be dimensioned and positioned so that the resistance between them varies within an acceptable operating range.

The implementations in FIGS. 1-10 also illustrate examples of arrays that include a support structure with a layered structure on its surface and cells. Each cell includes a respective region of the surface and a respective part of the layered structure on the cell's region. The part of the layered structure of at least one cell includes a passive electronic device as described above.

The implementations in FIGS. 1-10 also illustrate examples of a method that produces apparatus with a layered structure on a surface of a support structure, and producing the apparatus includes producing a passive electronic device with part of a first layer and one or more parts of a second layer as described above. The method includes, in producing the part of the first layer and the parts of the second layer, performing a printing operation.

In specific implementations, the method can print a mask over a deposited layer of material, then remove the exposed part of the deposited layer, leaving a part. The method can also deposit a layer of material over a printed mask, then perform a liftoff operation on the mask to remove part of the deposited layer, leaving a part. The method can print a patterned layer of material.

The exemplary implementations described above involve calorimeters and calorimeter and nanocalorimeter arrays, which could be applied in many ways. More specifically, implementations can be applied in nanocalorimeters and nanocalorimeter arrays that enable measurement of enthalpic changes, such as enthalpic changes arising from reactions, phase changes, changes in molecular conformation, and the like. Furthermore, combinatorial methods and high-throughput screening methods can use such nanocalorimeters in the study, discovery, and development of new compounds, materials, chemistries, and chemical processes, as well as high-throughput monitoring of compounds or materials, or high-throughput monitoring of the processes used to synthesize or modify compounds or materials.

The techniques described above in relation to FIGS. 1-10 are advantageous because they make it possible to replace photolithography with printing in producing structures as described above. For example, various layers can be patterned by direct printing or with printed masks, whether used as etch masks, liftoff masks, or both. Printing can dramatically reduce the number of fabrication steps and is especially appropriate for thermal sensors or other devices with passive components on flexible substrates. Fabrication yield can be increased, resolution can be improved, and cost can be reduced. Thermal sensing devices with lower 1/f noise can be produced. Fewer manual steps are required, making fabrication more feasible and cheaper.

The exemplary implementations described above are illustrated with specific shapes, dimensions, and other characteristics, but the scope of the invention includes various other shapes, dimensions, and characteristics. For example, the particular shapes of parts of patterned layers could be different, and could be of appropriate sizes for any particular type of passive electronic device. Also, spacings between components produced as described above can be less than the printed line width, allowing for features such as channel lengths that are smaller than the printed line width. Furthermore, rather than being thermistors or contacts as described above, the electronic devices as described above could be passive devices manufactured in various other ways for other types of applications and could include various other materials.

Similarly, the exemplary implementations described above include specific examples of printed patterned artifacts, but various other artifacts could occur as a result of printing. Further, the above exemplary implementations employ specific types of printing, but a wide variety of other printing techniques could be used within the scope of the invention.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A passive electronic device comprising:
   part of a first layer that includes electrically conductive or semiconductive material; the part of the first layer having a contact surface; and
   in electrical contact with the contact surface, one or more parts of a second layer that includes electrically conductive material; a subset of one or more of the parts of the second layer being electrically connectible to external circuitry;
   the first and second layers being within a layered structure on a support surface, at least one of the parts of the first and second layers including one or more printed patterned artifacts;
   in operation of the device, information being electrically transferred without gain or control between the external circuitry and the part of the first layer through at least one of the subset of parts of the second layer.

2. The device of claim 1 in which the first layer includes resistive semiconductive material.

3. The device of claim 2 in which the second layer includes electrically conductive metal.

4. The device of claim 1 in which the first and second layers both include electrically conductive metal.

5. The device of claim 1 in which the external circuitry includes a contact pad within the layered structure, one of the subset of parts of the second layer being electrically connected to the contact pad.

6. The device of claim 1 in which the external circuitry includes a pogo pin external to the layered structure, the subset of parts of the second layer including a contact pad that can be electrically contacted by the pogo pin.

7. The device of claim 1 in which the printed patterned artifacts include at least one of liftoff artifacts, masked etch artifacts, and direct printing artifacts.

8. The device of claim 7 in which the printed patterned artifacts include an uneven boundary portion of a part of one of the first and second layers.

9. The device of claim 7 in which the printed patterned artifacts include alignment of a part of one of the first and second layers with a position of a lower layer or with an alignment mark or alignment structure.

10. The device of claim 1 in which the device is a resistive device, the part of the first layer being a resistive component, the subset of parts of the second layer including first and second leads in electrical contact with the resistive component at first and second areas of the contact surface, the first and second areas being spaced apart in a direction across the contact surface.

11. The device of claim 10 in which the resistance of the resistive component between the first and second leads varies in response to non-electrical stimuli, the information that is electrically transferred indicating detection of the non-electrical stimuli.

12. The device of claim 1 in which the device is a conductive device, the part of the first layer being a conductive component, the subset of parts of the second layer including a metal contact pad in electrical contact with the conductive component over substantially the entire contact surface.

13. The device of claim 12 in which the first layer includes a stack of conductive metal sublayers and the second layer includes an adhesion sublayer on the contact surface and a gold sublayer on the adhesion sublayer.

14. The device of claim 1 in which both of the parts of the first and second layers each include one or more patterned printed layer artifacts.

15. The device of claim 1 in which the part of the first layer has a respective shape resulting from direct jet printing or from a jet printed mask and each of the parts of the second layer has a respective shape resulting from direct jet printing or from a jet printed mask.

16. A passive electronic device comprising:
part of a first layer that includes semiconductive material; the part of the first layer being resistive and having a contact surface; and
first and second parts of a second layer that includes electrically conductive material; each of the first and second parts of the second layer including:
a respective set of two or more substantially parallel lines that extend across and are in electrical contact with the contact surface; and
a connecting part that is not in contact with the contact surface but that electrically connects the respective set of lines;
the sets of lines of the first and second parts of the second layer being interdigitated;
the first and second layers being within a layered structure on a support surface, the part of the first layer and the first and second parts of the second layer each including one or more respective printed patterned artifacts;
in operation of the device, information being electrically transferred without gain or control to or from the part of the first layer through at least one of the first and second parts of the second layer.

17. The device of claim 16 in which the resistance of the part of the first layer between the first and second parts of the second layer varies in response to non-electrical stimuli; the first and second parts of the second layer allowing electrical detection of the non-electrical stimuli by electrical circuitry connected across the first and second parts.

18. The device of claim 17 in which the first and second parts of the second layer are dimensioned and positioned so that the resistance between them varies within an acceptable operating range.

19. The device of claim 16 in which the printed patterned artifacts include an uneven boundary portion of a part of one of the first and second layers.

20. The device of claim 16 in which the printed patterned artifacts include alignment of a part of one of the first and second layers with a position of a lower layer or with an alignment mark or alignment structure.

21. The device of claim 16 in which the part of the first layer has a respective shape resulting from direct jet printing or from a jet printed mask and each of the first and second parts of the second layer has a respective shape resulting from direct jet printing or from a jet printed mask.

22. An array comprising:
a support structure with a surface;
a layered structure on the surface; and
one or more cells, each cell including:
a respective region of the surface; and
a respective part of the layered structure on the cell's region of the surface; the respective part of at least one cell including a passive electronic device that includes:
part of a first layer that includes electrically conductive or semiconductive material; the part of the first layer having a contact surface; and
in electrical contact with the contact surface, one or more parts of a second layer that includes electrically conductive material; a subset of one or more of the parts of the second layer being electrically connectible to external circuitry;
at least one of the parts of the first and second layers including one or more printed patterned artifacts;
in operation of the passive electronic device, information being electrically transferred without gain or control between the external circuitry and the part of the first layer through at least one of the subset of parts of the second layer.

23. The array of claim 22 in which the support structure includes a polymer layer.

24. The array of claim 22 in which the printed patterned artifacts include an uneven boundary portion of a part of one of the first and second layers.

25. The array of claim 22 in which the printed patterned artifacts include alignment of a part of one of the first and second layers with a position of a lower layer or with an alignment mark or alignment structure.

26. The array of claim 22 in which the part of the first layer has a respective shape resulting from direct jet printing or from a jet printed mask and each of the parts of the second layer has a respective shape resulting from direct jet printing or from a jet printed mask.

27. A device on a support surface, the device comprising:
first, second, third, and fourth resistive thermal sensors; in use, the first and second thermal sensors receiving a first thermal signal and the third and fourth thermal sensors receiving a second thermal signal;
first, second, third, and fourth contact pads;
a set of electrically conductive leads that connect the thermal sensors and the contact pads so that the first, second, third, and fourth contact pads can be connected into a Wheatstone bridge circuit that would be balanced if resistances of the first and second thermal sensors were the same as resistances of the third and fourth thermal sensors;
a first patterned layer that includes semiconductive material deposited over the support surface; each of the first, second, third, and fourth thermal sensors including a respective semiconductive slab that is part of the first patterned layer, that is resistive, that has a respective surface, and that has a shape resulting from direct jet printing or from a jet printed mask; the shape including first and second straight boundaries;

a second patterned layer that includes electrically conductive material deposited over the support surface; each of the first, second, third, and fourth thermal sensors including respective first and second sets of digit lines that are parts of the second patterned layer; each of the first, second, third, and fourth contact pads including a respective contact body that is part of the second patterned layer; each of the set of leads being part of the second patterned layer; each of the digit lines, contact bodies, and leads having a shape resulting from direct jet printing or from a jet printed mask; and a third patterned layer that includes highly electrically conductive material; each of the first, second, third, and fourth contact pads including a respective highly conductive contact part that, in use, provides ohmic contact between the respective contact body and external circuitry, the highly conductive contact part being part of the third patterned layer; the highly conductive contact part having a shape resulting from direct jet printing or from a jet printed mask;

the set of leads including first, second, third, and fourth leads, connected to the respective contact bodies of the first, second, third, and fourth contact pads, respectively, and each extending around the first straight boundary of the respective slab of one of the thermal sensors and connecting to the respective first set of digit lines and around the second straight boundary of the respective slab of another of the thermal sensors and connecting to the respective second set of digit lines so that each slab has a respective first lead part around its first straight boundary and a respective second lead part around its second straight boundary; each digit line in each slab's first set of digit lines extending from around the slab's first straight boundary across the surface of the slab; each digit line in each slab's second set of digit lines extending from around the second straight boundary across the surface of the slab; each of the digit lines in the first and second sets being in electrical contact with the surface of the slab; the first and second sets of digit lines being interdigitated;

when connected into a Wheatstone bridge in use, information being electrically transferred between the external circuitry and the respective slabs of the thermal sensors through the contact pads, the set of leads, and the digit lines without gain or control.

* * * * *